(12) United States Patent
Ding et al.

(10) Patent No.: US 8,764,981 B2
(45) Date of Patent: Jul. 1, 2014

(54) DIALYSIS TREATMENT DEVICES FOR REMOVING UREA

(75) Inventors: Yuanpang Samuel Ding, Libertyville, IL (US); Ying-Cheng Lo, Green Oak, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 108 days.

(21) Appl. No.: 13/296,522

(22) Filed: Nov. 15, 2011

(65) Prior Publication Data

US 2012/0055864 A1 Mar. 8, 2012

Related U.S. Application Data

(62) Division of application No. 12/482,869, filed on Jun. 11, 2009, now Pat. No. 8,080,161.

(51) Int. Cl.
| | |
|---|---|
| *B01D 61/30* | (2006.01) |
| *A61M 1/14* | (2006.01) |
| *A61M 37/00* | (2006.01) |
| *A61M 1/28* | (2006.01) |
| *A61M 1/16* | (2006.01) |

(52) U.S. Cl.
CPC .............. *B01D 61/30* (2013.01); *A61M 1/287* (2013.01); *A61M 1/1696* (2013.01)
USPC ...................................... 210/321.71; 210/648

(58) Field of Classification Search
None
See application file for complete search history.

(56) References Cited

U.S. PATENT DOCUMENTS

| | | |
|---|---|---|
| 2002/0112609 A1 | 8/2002 | Wong |
| 2004/0019312 A1 | 1/2004 | Childers et al. |
| 2005/0274658 A1 | 12/2005 | Rosenbaum et al. |
| 2007/0179431 A1 | 8/2007 | Roberts et al. |
| 2008/0051696 A1 | 2/2008 | Curtin et al. |
| 2009/0114595 A1 | 5/2009 | Wallenas et al. |
| 2009/0127193 A1 | 5/2009 | Updyke et al. |

FOREIGN PATENT DOCUMENTS

| | | |
|---|---|---|
| WO | 2007/089855 | 8/2007 |
| WO | 2007/103411 | 9/2007 |

OTHER PUBLICATIONS

International Search Report for PCT/US2010/033482 date mailed Aug. 27, 2010, 8 pages.
Written Opinion of the International Searching Authority for PCT/US2010/033482 date mailed Aug. 27, 2010, 7 pages.
Manns et al., The acu-menTM: A new device for continuous renal replacement therapy in actue renal failure, Kidney International, 1998, pp. 268-274, vol. 54.
Japanese Office Action for Japanese Application No. P2012-514961, dated Feb. 4, 2014.

*Primary Examiner* — Krishnan S Menon
(74) *Attorney, Agent, or Firm* — K&L Gates LLP

(57) ABSTRACT

Dialysis treatment devices and methods for removing urea from dialysis waste streams are provided. In a general embodiment, the present disclosure provides a dialysis treatment device including: 1) a first filter having a filtration membrane, 2) a urea removal unit having urease and in fluid communication with the first filter, and 3) a second filter having an ion rejection membrane and in fluid communication with the first filter and the urea removal unit.

15 Claims, 3 Drawing Sheets

DIALYSIS TREATMENT DEVICES FOR REMOVING UREA

CROSS REFERENCE TO RELATED APPLICATIONS

This application is a divisional of U.S. patent application Ser. No. 12/482,869 filed Jun. 11, 2009, the entire contents of which are herein incorporated by reference in their entirety.

BACKGROUND

The present disclosure is in the general field of dialysis treatment devices and methods, and in particular, for removing urea from dialysis waste streams.

Hemodialysis and peritoneal dialysis are two types of dialysis therapies used commonly to treat loss of kidney function. A hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, through the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, dialysis systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia (e.g. ammonium cation). The ammonia is then removed from the dialysate by adsorption prior to reintroduction of the dialysate into the peritoneal cavity. Additional sensors are employed to monitor the removal of ammonia. CFPD systems are typically more complicated than batch systems.

In both hemodialysis and peritoneal dialysis, "sorbent" technology can be used to remove uremic toxins from waste dialysate, re-inject therapeutic agents (such as ions and/or glucose) into the treated fluid, and reuse that fluid to continue the dialysis of the patient. One commonly used sorbent is made from zirconium phosphate, which is used to remove ammonia generated from the hydrolysis of urea. Typically, a large quantity of sorbent is necessary to remove the ammonia generated during dialysis treatments.

The main advantage of the sorbent based approach is that very low volumes of water are required to achieve high volume dialysis treatments. The main disadvantage of the sorbent system is the high cost of the sorbent disposable, the amount of space required to house the sorbent, and concerns regarding the purity of the recycled solution, as many ions remain in the fluid after treatment and verification of purity is technically challenging to perform.

SUMMARY

The present disclosure provides dialysis treatment devices and methods that treat dialysis waste streams during hemodialysis and peritoneal dialysis. In a general embodiment, the present disclosure provides a dialysis treatment device including: 1) a first filter having a filtration membrane, 2) a urea removal unit having urease and in fluid communication with the first filter, and 3) a second filter having an ion rejection membrane and in fluid communication with the first filter and the urea removal unit.

In an embodiment, the dialysis treatment device includes a flow restrictor positioned between the first filter and the second filter. The dialysis treatment device can be contained within a cartridge for a wearable kidney. The cartridge can be configured to be removable and/or disposable.

In a further alternative embodiment, the present disclosure provides a dialysis treatment device including: 1) a filter having an adsorption layer, a filtration membrane and an ion exchange sorbent, and 2) a urea removal unit in fluid communication with the filter. The urease removal unit can include a urease layer, an ammonia sorbent layer and an ion rejection membrane.

It is accordingly an advantage of the present disclosure to provide an improved dialysis treatment device.

It is another advantage of the present disclosure to provide an improved urea removal cartridge.

It is yet another advantage of the present disclosure to provide a sorbentless urea removal cartridge for a wearable kidney.

Still further, it is an advantage of the present disclosure to provide a urea removal cartridge for a wearable kidney having a reduced ammonia sorbent requirement.

Another advantage of the present disclosure to provide an improved method for removing urea from a dialysis waste stream.

Additional features and advantages are described herein, and will be apparent from the following Detailed Description and the figures.

DETAILED DESCRIPTION

The present disclosure relates to dialysis treatment devices and methods for removing urea from dialysis waste streams during hemodialysis or peritoneal dialysis. In a general embodiment, the dialysis treatment devices are constructed and arranged to require no sorbents for trapping ammonia generated by the hydrolysis of urea by urease. In another embodiment, the dialysis treatment devices are constructed and arranged to significantly reduce the amount of sorbent necessary for removing urea from the dialysis waste stream. This can significantly reduce the cost, size and complexity of dialysis treatments systems that remove urea.

The dialysis treatment devices and methods can be used and implemented in various hemodialysis and peritoneal dialysis technologies such as, for example, those described in U.S. Pat. Nos. 5,244,568, 5,350,357, 5,662,806, 6,592,542 and 7,318,892, which are incorporated herein by reference. The hemodialysis and peritoneal dialysis technologies can be designed and configured for medical centers and be implemented with on-site or at-home dialysis treatments. The dialysis treatment devices and methods can further be used in portable dialysis treatment devices such as, for example, wearable artificial kidneys in which a patient may move freely during dialysis. Non-limiting examples of portable dialysis treatment devices are described in U.S. Pat. Nos. 5,873,853, 5,984,891 and 6,196,992 and U.S. Patent Publication Nos. 2007/0213665 and 2008/0051696, which are incorporated herein by reference.

Figure 1:
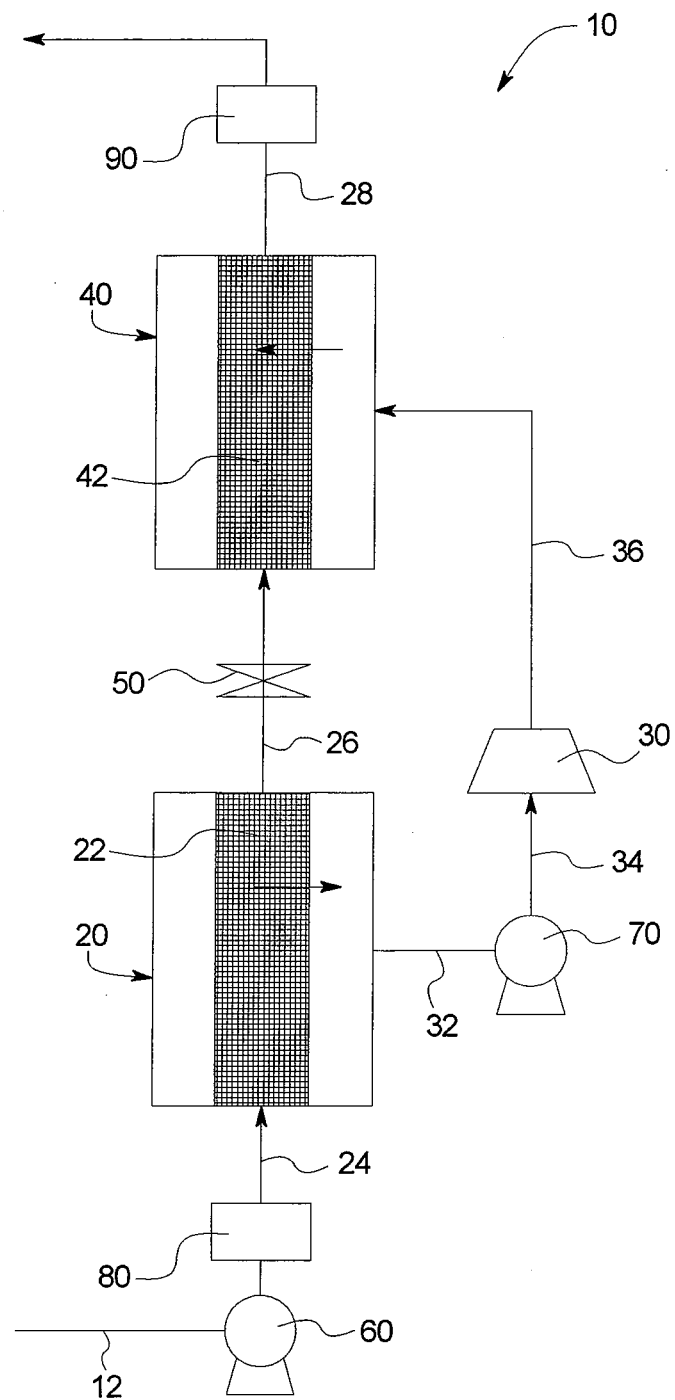
FIG. 1 is a schematic illustration of a dialysis treatment device using multiple filters in an embodiment of the present disclosure.

Referring now to the drawings and in particular to FIG. 1, one embodiment of a dialysis treatment device 10 of the present disclosure is illustrated. Dialysis treatment device 10 includes a first filter 20, a urea removal unit 30, and a second filter 40. In this configuration, urea removal unit 30 is a separate component from the filters. Dialysis treatment device 10 can further include a constriction partition or flow restrictor 50 positioned between first filter 20 and second filter 40. Dialysis treatment device 10 can be sized and configured to be contained within a treatment cartridge for a portable dialysis treatment devices such as, for example, wearable kidneys. The treatment cartridge in such cases can be disposable or reusable.

First filter 20 has a filtration membrane 22. Filtration membrane 22 can be, for example, in the form of a hollow fiber cartridge with a membrane skin. The membrane can designed to allow very small molecules (e.g. urea) to pass through while retaining charged and larger molecules. Suitable membranes that can be used as filtration membrane 22 include nanofiltration membranes or reverse osmosis membranes. An example of a nanofiltration membrane is described in WO Publication No. 2004/009158, which is incorporated herein by reference. In addition, an ion coating can be added to nanofiltration membranes or reverse osmosis membranes used as filtration membrane 22 to further trap or exchange ionic compounds in the dialysis waste stream.

In another embodiment, filtration membrane 22 of first filter 20 is a cation rejection membrane or anion rejection membrane. Ion-rejection membrane 22 can be designed to allow the passage of negatively charged ions and nonionic species, but restrict the passage of specific positively charged ions. Alternatively, ion-rejection membrane 22 can allow the passage of positively charged ions and nonionic species, but restrict the passage of specific negatively charged ions.

Urea removal unit 30 contains urease, an enzyme that catalyzes the hydrolysis of urea into carbon dioxide (e.g. bicarbonate) and ammonia (e.g. ammonium cation). Urea from the dialysis waste stream is exposed to the urease at this location. The urease can be contained in urea removal unit 30 in any suitable manner. For example, the urease can be immobilized in a layer of beads or resins or be cross-linked urease enzyme crystals impregnated as part of a membrane. Urea removal unit 30 is in fluid communication with first filter 20 via a flow path 32. Flow path 32, and indeed any of the flow paths described herein, can be provided as a length of tubing or as a flow path defined in a rigid and/or flexible, disposable or reusable cassette.

In an alternative embodiment, urea removal unit 20 can be integral with first filter 20. For example, immobilized urease can be placed outside the hollow fibers of ion rejection membrane 22.

Second filter 40 has an ion rejection membrane 42 and is in fluid communication with first filter 20 via a flow path 26 and urea removal unit 30 via a flow path 36. In different embodiments, ion rejection membrane 42 of second filter 40 can be a cation rejection membrane or an anion rejection membrane. In another embodiment, ion rejection membrane 42 of second filter 40 is a reverse osmosis membrane.

In an alternative embodiment, dialysis treatment device 10 includes an adsorption or carbon chamber 80 in fluid communication with first filter 20. In this manner, organic toxins of the dialysis waste stream can be removed from the waste stream prior to entering first filter 20 through adsorption onto an adsorption layer surface of the carbon (e.g., activated carbon or other appropriate organic neutralizing surface).

In another embodiment, dialysis treatment device 10 includes a supplementary ammonia sorbent unit 90 in fluid communication with second filter 40 as a precautionary measure to completely remove any ammonia from the fluid that passes through dialysis treatment device 10. The ammonia sorbent unit can include, for example, zirconium phosphate to trap any residual ammonia in the treated fluid stream.

As seen in FIG. 1, a pump 60 causes a fluid flow path 12 of spent dialysis or a dialysis waste stream from a patient to enter first filter 20 via a flow path 24. The dialysis waste stream may or may not have been treated, for example, using activated carbon prior to entering dialysis treatment device 10. A pump 70 transports fluid from first filter 20 to urea removal unit 30 via flow paths 32 and 34. Filtration membrane 22 may be capable of retaining charged species such as $Ca^{2+}$, $Mg^{2+}$, $Na^+$ and proteins within first filter 20, which flow into second filter 40 via flow path 26. As a result, a fluid stream composed primarily of water and urea flows to urea removal unit 30.

Urea removal unit 30 converts urea to ammonia and carbon dioxide, which travel to second filter 40 via flow path 36. Second filter 40 can provide a hollow fiber cation rejection membrane as ion rejection membrane 42. As a result, the ammonia remains trapped outside of ion rejection membrane 42 and does not proceed through flow path 28. To improve the treatment capacity of dialysis treatment device 10, flow path 36 between urea removal unit 30 and second filter 40 should be sufficiently long enough to prevent the urease contained in urea removal unit 30 from being saturated with ammonia.

The final treated dialysate stream exits second filter 40 via flow path 28 for further use or treatment (e.g., ion exchange) and then back to the patient. In addition, ions and/or fluids can be replaced in the stream, for example, through the addition of concentrated dialysis components such as osmotic agents (e.g., dextrose, icodextrin, glucose polymers, glucose polymer derivatives, amino acids), buffers (e.g., lactate, bicarbonate) and electrolytes (e.g., sodium, potassium, calcium, magnesium) from a suitable fluid source.

In an alternative embodiment, flow restrictor 50 and/or pump 70 can be used to create high pressure gradients in first filter 20 and/or second filter 40. In this regard, flow restrictor 50 and/or pumps 60 and 70 can provide a sufficiently high pressure to force fluid through filtration membrane 22 and out of first filter 20 via flow paths 32 and 34.

Figure 2:
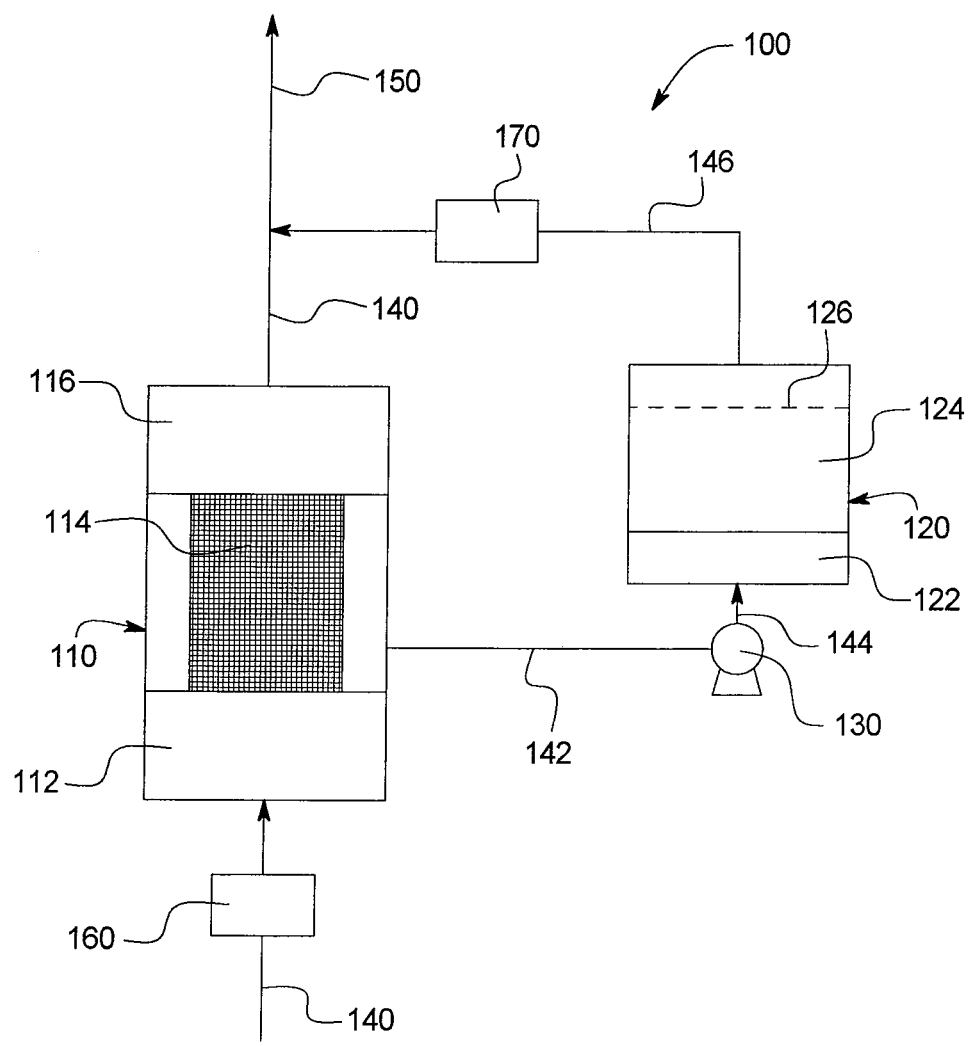
FIG. 2 is a schematic illustration of a dialysis treatment device in a third embodiment of the present disclosure.

In another embodiment illustrated in FIG. 2, a dialysis treatment device 100 includes a filter 110 and a urea removal unit 120 in fluid communication with filter 110 via flow paths 142 and 144. A pump 130 can be positioned between filter 110 and urea removal unit 120 to facilitate flow between the two components. Dialysis treatment device 100 can be sized and configured to be contained within a treatment cartridge for any of the above-listed type of dialysis treatment devices.

Filter 110 can include an adsorption layer 112, a filtration membrane 114 and an ion exchange sorbent 116. Adsorption layer 112 can be, for example, carbon. In this manner, organic toxins of the dialysis waste stream can be removed from the waste stream through adsorption onto the adsorption layer surface.

Filtration membrane 114 can be, for example, in the form of a hollow fiber cartridge with a membrane skin that is designed to allow very small molecules to pass through while retaining charged and larger molecules. Suitable membranes that can be used as filtration membrane 114 include nanofiltration membranes or reverse osmosis membranes. Alternatively, filtration membrane 114 of filter 110 can be a cation rejection membrane or an anion rejection membrane. In an embodiment, ion exchange sorbent 116 is an anion exchange sorbent to remove anions such as, for example, phosphate and sulfate.

Urea removal unit 120 can include a urease layer 122, an ammonia sorbent layer 124 and an ion rejection membrane 126. Ion rejection membrane 126 can be a cation rejection membrane. The urease can be contained in urea removal unit 120 in any suitable manner. As illustrated in FIG. 2, the treated dialysis fluid from urea removal unit 120 in flow path 146 can combine with the treated dialysate fluid from filter 110 in flow path 140 to form a combined treated fluid flow path 150 for subsequent treatment/recirculation. In another embodiment, ion rejection membrane 126 is a reverse osmosis membrane.

In an alternative embodiment, dialysis treatment device 100 includes an adsorption or carbon chamber 160 in fluid communication with filter 110. In this manner, organic toxins of the dialysis waste stream can be removed from the waste stream prior to entering filter 110 through adsorption onto an adsorption layer surface of the carbon (e.g., activated carbon or other appropriate organic neutralizing surface).

In another embodiment, dialysis treatment device 100 includes a supplementary ammonia sorbent unit 170 in fluid communication with at least one of filter 110 and urea removal unit 120 as a precautionary measure to completely remove any ammonia from the fluid that passes through dialysis treatment device 100. Ammonia sorbent unit 170 can include, for example, zirconium phosphate to trap any residual ammonia in the treated fluid stream.

Due to the design of dialysis treatment devices 10 and 100, sorbents such as zirconium phosphate, zirconium bicarbonate and/or ion exchange layers typically used for ammonia removal may be unnecessary. Alternatively, dialysis treatment devices 10 and 100 allow for a reduced amount of sorbent necessary as compared to typical dialysis treatment systems using sorbents for ammonia removal.

Figure 3A:
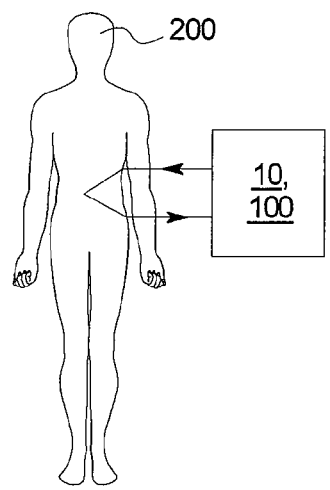
FIGS. 3A to 3D are schematic illustrations of the dialysis treatment devices used in various dialysis treatment technologies.

Any of the dialysis treatment devices 10 and 100 discussed herein can be used for peritoneal dialysis ("PD"), hemodialysis ("HD"), hemofiltration ("HF") or hemodiafiltration ("HDF") as shown in FIGS. 3A-3D, respectively. FIG. 3A illustrates a schematic of a PD treatment being performed on a patient 200. Spent dialysis fluid from patient 200 enters one of dialysis treatment devices 10 and 100 for treatment/urea removal. Regenerated dialysis is returned to the patient for reuse. This can be done on a continuous basis ("CFPD"), on a batch basis in which dialysis fluid dwells within patient 200 for a period of time, or on a semi-continuous or tidal basis.

Figure 3B:
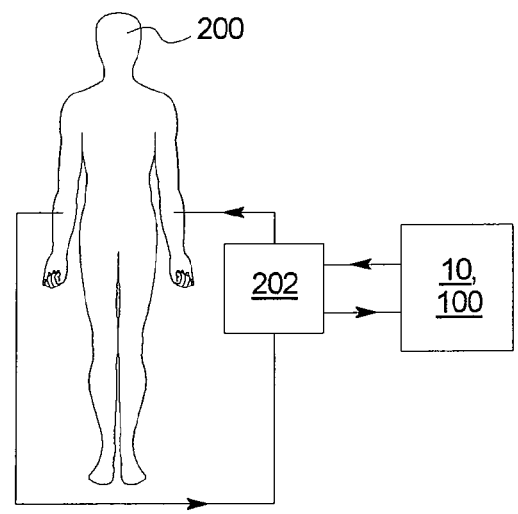

FIG. 3B illustrates a schematic of an HD treatment being performed on patient 200. Blood from patient 200 is pumped through a dialyzer 202, cleaned and returned to patient 200. Spent dialysis fluid from dialyzer 202 is sent to one of the dialysis treatment device 10 or 100 for treatment/urea removal. The treated fluid is then returned to dialyzer 202 on a continuous basis to continuously clean the patients' blood.

Figure 3C:
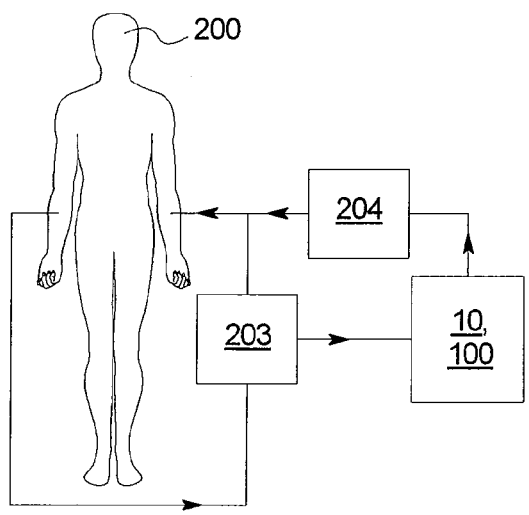

FIG. 3C illustrates a schematic of an HF treatment technology. HF is a technology similar to HD. With hemofiltration, dialysate is not used. Instead, a positive hydrostatic pressure drives water and solutes across the filter membrane of hemofilter 203 from its blood compartment to its filtrate compartment, from which it is drained. The spent dialysis fluid is sent to one of the dialysis treatment devices 10 or 100 for treatment/urea removal. The treated fluid is then further purified by being sent through one or more pyrogen filters 204 such as an ultrafilter, pyrogen filter or nanofilter that removes toxins and endotoxins. The resulting replacement fluid is pumped directly into the blood causing a corrective cleansing of the patient. As with PD and HD, a net volume of fluid is taken out of the patient as ultrafiltrate to remove excess water that the patient has accumulated between treatments.

Figure 3D:
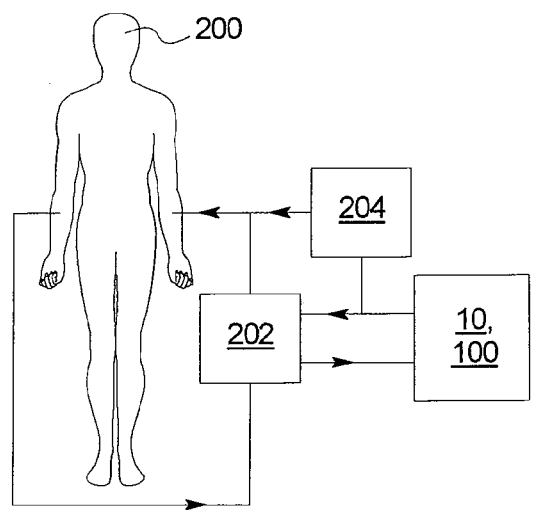

FIG. 3D illustrates a schematic of an HDF treatment technology. HDF is a combination of HD and HF. Blood is pumped through the blood compartment of dialyzer 202 in a manner similar to HD and HF. A high rate of ultrafiltration is used, so there is a high rate of movement of water and solutes from the blood to the dialysate that is replaced by a return of cleansed dialysate dialyzer 202 and substitution fluid that is infused again through one or more of a pyrogen filter, nanofilter, or ultrafilter directly into the patient's blood line. HDF results in good removal of both large and small molecular weight solutes. Treatment devices 10 and 100 regenerate spent fluid from dialyzer 202 for both delivery back to dialyzer 202 and to the patient's blood line directly via ultrafilter 204.

In alternative embodiments, the present disclosure provides methods comprising circulating a dialysis fluid in a fluid circuit of a dialysis technology or apparatus incorporating one or more of the dialysis devices in the form of a sorbentless or reduced sorbent cartridge. The dialysis apparatus can be a wearable dialysis device.

The spent dialysis fluid contains wastes from a treated patient. The spent dialysis fluid can be sent to the dialysis technology and wastes such as urea are removed using the cartridge. The treated fluid can then be recirculated back to the patient for further use.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis treatment device comprising:
   a filter comprising an adsorption layer, a filtration membrane and an ion exchange sorbent; and
   a urea removal unit in fluid communication with a filtrate stream of the filter, the urea removal unit comprising a urease layer, an ammonia sorbent layer and an ion rejection membrane.

2. The dialysis treatment device of claim 1, wherein the dialysis treatment device is contained within a cartridge for a wearable kidney.

3. The dialysis treatment of claim 1, wherein the ion exchange sorbent is an anion exchange sorbent, and wherein the ion rejection membrane is a cation rejection membrane or a reverse osmosis membrane.

4. The dialysis treatment device of claim 1 further comprising a pump positioned between the filter and the urea removal unit.

5. The dialysis treatment device of claim 1 further comprising an activated carbon unit in fluid communication with the filter.

6. The dialysis treatment device of claim 3, wherein the reverse osmosis membrane includes an ion coating to trap ionic compounds.

7. The dialysis treatment device of claim 1 further comprising a zirconium phosphate layer in fluid communication with at least one of the filter and the urea removal unit.

8. A dialysis treatment device comprising:
   a filter that produces a first treated dialysis fluid in a first flow path, the filter including an adsorption layer, a filtration membrane and an ion exchange sorbent; and
   a urea removal unit that produces a second treated dialysis fluid, the urea removal unit in fluid communication with a filtrate stream of the filter via a second flow path, the urea removal unit including a urease layer, an ammonia sorbent layer and an ion rejection membrane, and
   wherein the first and second flow paths combine in a third flow path to form a combined treated fluid for subsequent treatment and/or recirculation.

9. The dialysis treatment device of claim 8, which is contained within a cartridge for a wearable kidney.

10. The dialysis treatment of claim 8, wherein the ion exchange sorbent is an anion exchange sorbent, and wherein the ion rejection membrane is a cation rejection membrane or a reverse osmosis membrane.

11. The dialysis treatment device of claim 8, wherein the second flow path includes a pump.

12. The dialysis treatment device of claim 8, which further includes an activated carbon unit in fluid communication with the filter.

13. The dialysis treatment device of claim 10, wherein the reverse osmosis membrane includes an ion coating to trap ionic compounds.

14. The dialysis treatment device of claim 8, which further includes a zirconium phosphate layer in fluid communication with at least one of the filter and the urea removal unit.

15. The dialysis treatment device of claim 8, wherein the second flow path includes a supplementary ammonia sorbent unit between the urea removal unit and the third flow path.

* * * * *